(12) United States Patent
Marotta

(10) Patent No.: US 11,054,419 B2
(45) Date of Patent: Jul. 6, 2021

(54) COMPOSITIONS AND METHODS FOR CHARACTERIZING ARTHRITIC CONDITIONS

(76) Inventor: Anthony Marotta, Burnaby (CA)

( * ) Notice: Subject to any disclaimer, the term of this patent is extended or adjusted under 35 U.S.C. 154(b) by 1006 days.

(21) Appl. No.: 13/255,873

(22) PCT Filed: Mar. 11, 2010

(86) PCT No.: PCT/CA2010/000368
§ 371 (c)(1),
(2), (4) Date: Nov. 18, 2011

(87) PCT Pub. No.: WO2010/102412
PCT Pub. Date: Sep. 16, 2010

(65) Prior Publication Data
US 2012/0058498 A1    Mar. 8, 2012

Related U.S. Application Data

(60) Provisional application No. 61/159,386, filed on Mar. 11, 2009.

(51) Int. Cl.
*G01N 33/564* (2006.01)

(52) U.S. Cl.
CPC ..... *G01N 33/564* (2013.01); *G01N 2800/102* (2013.01)

(58) Field of Classification Search
CPC .................. G01N 33/564; G01N 2800/102
See application file for complete search history.

(56) References Cited

U.S. PATENT DOCUMENTS

| | | | | |
|---|---|---|---|---|
| 4,956,281 A * | 9/1990 | Wallner | ............ | G01N 33/56972 435/252.31 |
| 5,948,765 A | 9/1999 | Shaw et al. | | |
| 5,976,852 A | 11/1999 | Cheng et al. | | |
| 5,998,149 A | 12/1999 | Hsich et al. | | |
| 6,596,476 B1 * | 7/2003 | Lesniewski et al. | ............ | 435/5 |
| 7,011,952 B2 * | 3/2006 | Hageman et al. | ............ | 435/7.21 |
| 7,056,677 B2 | 6/2006 | Takahasi et al. | | |
| 7,101,962 B2 | 9/2006 | Burke et al. | | |
| 7,171,311 B2 | 1/2007 | Dai et al. | | |
| 7,396,654 B2 | 7/2008 | Hayes et al. | | |
| 7,919,262 B2 | 4/2011 | Yacoubian et al. | | |
| 7,939,272 B2 | 5/2011 | Buck | | |
| 2002/0173454 A1 * | 11/2002 | Rosen | ..................... | C07K 14/47 435/6.16 |
| 2003/0109420 A1 * | 6/2003 | Valkirs | ..................... | G01N 33/53 435/7.1 |
| 2003/0119054 A1 * | 6/2003 | Mrksich | ................. | B82Y 30/00 435/7.1 |
| 2004/0152630 A1 | 8/2004 | Fu et al. | | |
| 2005/0009094 A1 | 1/2005 | Mueller | | |
| 2005/0042681 A1 | 2/2005 | Van Eyk et al. | | |
| 2008/0220013 A1 | 9/2008 | Hochstrasser et al. | | |
| 2009/0093005 A1 | 4/2009 | Smalley et al. | | |
| 2010/0016173 A1 | 1/2010 | Nagalla et al. | | |
| 2011/0027269 A1 * | 2/2011 | Marrotta | ................. | C07K 16/18 424/133.1 |
| 2011/0052573 A1 | 3/2011 | Marotta | | |
| 2012/0077695 A1 | 3/2012 | Ostroff et al. | | |
| 2012/0101002 A1 | 4/2012 | Riel-Mehan et al. | | |
| 2016/0185842 A1 * | 6/2016 | Marotta | ................. | C07K 16/18 424/133.1 |

FOREIGN PATENT DOCUMENTS

| | | | |
|---|---|---|---|
| JP | 2005-181342 A | 7/2005 | |
| KR | 10-2002-0061794 | 7/2002 | |
| WO | WO 1997/33601 A1 | 9/1997 | |
| WO | WO 1997/38315 A1 | 10/1997 | |
| WO | WO 1998/026293 A1 | 6/1998 | |
| WO | WO 2003/071927 A2 | 9/2003 | |
| WO | WO 2003/087831 A2 | 10/2003 | |
| WO | WO 2005/053811 A2 | 6/2005 | |
| WO | WO 2005/120568 A1 | 12/2005 | |
| WO | WO 2006/126008 A2 * | 11/2006 | |
| WO | WO 2007/128132 A1 * | 11/2007 | ........... G01N 33/564 |
| WO | WO2009067811 A1 * | 6/2009 | ............. C07K 16/18 |
| WO | WO2009067820 A1 * | 6/2009 | ........... A61K 39/395 |
| WO | WO 2009/137832 A2 * | 11/2009 | ........... G01N 33/574 |

OTHER PUBLICATIONS

Kilani et al. "Detection of High Levels of 2 Specific Isoforms of 14-3-3 Proteins in Synovial Fluid from Patients with Joint Inflammation" J Rheumatol 2007;34;1650-1657.*

Maksymowych et al., "Serum 14-3-3: A rheumatoid arthritis biomarker" Arthritis and Rheumatism, (Oct. 2011) vol. 63, No. 10, Supp. SUPPL. 1. Abstract No. 358, three pages.*

Harlow, E. and Lane, D., Antibodies: A Laboratory Manual (1988) Cold Spring Harbor Laboratory Press, Cold Spring Harbor, NY, pp. 23-26.*

Lyons et al. "Effective Use of Autoantibody Tests in the Diagnosis of Systemic Autoimmune Disease", Ann. N.Y. Acad. Sci. 1050:217-228 (2005).*

Sequence listing for Ghahary et al. (WO 2007/128132, of record), dated Jul. 11, 2007, 13 pages (retrieved from https ://patentscope.wipo.int/search/en/detail.jsf?docId=WO2007128132&recNum=1&tab=PCTDocuments&maxRec=&office=&prevFilter=&sortOption=&queryString= on Apr. 25, 2016).*

Rosenau et al. "Autoantibodies to Tumor Necrosis Factor in Patients with Rheumatoid Arthritis and Systemic Lupus Erythematosus" J Rheumatol 2009;36:753-6; doi:10.3899/jrheum.080587).*

Gabay et al. "Occurrence of antiperinuclear, antikeratin, and anti-RA 33 antibodies in juvenile chronic arthritis" Ann Rheum Dis. Nov. 1993; 52(11): 785-789.*

Maksymowych et al. "14-3-3η Autoantibodies: Diagnostic Use in Early Rheumatoid Arthritis", J Rheumatol. Sep. 2015;42(9): 1587-94. doi: 10.3899/jrheum.141385. Epub Jul. 15, 2015 (Year: 2015).*

Barcynska et al. "Coexistence of rheumatoid arthritis and ankylosing spondylitis", Reumatologia 2015; 53, 5: 279-285, DOI: 10.5114/reum.2015.55832 (Year: 2015).*

(Continued)

*Primary Examiner* — Christine Foster
(74) *Attorney, Agent, or Firm* — Todd A. Lorenz

(57) ABSTRACT

The present invention relates to autoantibodies against 14-3-3 proteins or circulating immune complexes thereof and the detection of such for the diagnosis and prognosis of an arthritic condition.

14 Claims, 4 Drawing Sheets

Specification includes a Sequence Listing.

(56) References Cited

OTHER PUBLICATIONS

Braun et al. "Classification criteria for rheumatoid arthritis and ankylosing spondylitis" Clin Exp Rheumatol. Jul.-Aug. 2009;27(4 Suppl 55):S68-73 (Year: 2009).*
Cao et al. "Clinical Significance of Combined Anti-Cyclic Citrullinated Peptide Antibody and Rheumatoid Factor Assays in Rheumatoid Arthritis Diagnosis"Arch Rheumatol 2015;30(2):104-108, doi: 10.5606/ArchRheumatol.2015.4318 (Year: 2015).*
Ahrens, D. et al., "Expression of matrix metalloproteinase 9 (96-kd gelatinase B) in human arthritis," Arthritis & Rheum. vol. 39, pp. 1576-1587 (1996).
Ausubel, F. et al., "Current Protocols in Molecular Biology", Ch. 1 Immunoassays, pp. 11.0.1-11.3.6, John Wiley & Sons, New York (1998).
Ausubel, F. et al., "Short Protocols in Molecular Biology", Ch. 11 Immunology, pp. 11-4-11-5, John Wiley & Sons, New York (1999).
Bombara, MP et al., "Cell contact between T cells and synovial fibroblasts causes induction of adhesion molecules and cytokines," J. Leukocyte Biol. vol. 54, pp. 339-406 (1993).
Boston, P. et al., "Human 14-3-3 Protein:Radioimmunoassay, Tissue Distribution, and Cerebrospinal Fluid Levels in Patients With Neurological Disorders,"J. N. Chem. vol. 38, pp. 1475-1482 (1982).
Brand, DD., "Rodent models of rheumatoid arthritis," Comp. Med., vol. 55(2), pp. 114-122 (2005).
Burger, D. et al., "Imbalance between interstitial collagenase and tissue inhibitor of metalloproteinases 1 in synoviocytes and fibroblasts upon direct contact with stimulated T lymphocytes: involvement of membrane-associated cytokines," Arthritis Rheum., vol. 41(10), pp. 1748-1759 (1998).
Chan, TA et al., "14-3-3Sigma is required to prevent mitotic catastrophe after DNA damage," Nature, vol. 401, pp. 616-620 (1999).
Cho, ML et al., "Effector function of type II collagen-stimulated T cells from rheumatoid arthritis patients: cross-talk between T cells and synovial fibroblasts," Arthritis Rheum., vol. 50(3), pp. 776-784 (2004).
Corconnier et al., "Diagnostic value of anti-RA33 antibody, antikeratin antibody, antiperinuclear factor and antinuclear antibody in early rheumatoid arthritis: comparison with rheumatoid factor," Br. J. Rheumatol., vol. 35, pp. 620-624 (1996).
Craparo, A. et al., "14-3-3 (ε) Interacts with the insulin-like growth factor I receptor and insulin receptor substrate I in a phosphoserine-dependent manner," J. Biol. Chem., vol. 272(17), pp. 11663-11669 (1997).
Daien, Claire I. and Morel, Jacques, "Predictive Factors of Response to Biological Disease Modifying Antirheumatic Drugs: Towards Personalized Medicine," Mediators of Inflammation, vol. 2014: 386148, pp. 1-11 (2014).
Da Silva et al., "Safety of low dose glucocorticoid treatment in rheumatoid arthritis: published evidence and prospective trial data," Ann. Rheum Dis., vol. 65, pp. 285-293 (2006).
Di Fede, G. et al., "The ε isoform of 14-3-3 protein is a component of the prion protein amyloid deposits of Gerstmann-Sträussler-Scheinker Disease," J. Neuropathology and Experimental Neurology, vol. 66(2), pp. 124-130 (2007).
Du et al., "Association of a phospholipase A2 (14-3-3 protein) with the platelet glycoprotein Ib-IX Complex," J. Biol. Chem., vol. 269(28), pp. 18287-18290.
Firestein, Gary S.,"Rheumatoid Arthritis: Rheumatoid Synovitis and Pannus," Rheumatology, pp. 5/13.1-5/13.5, Mosby, London (1997).
Frank, R. et al., "Spot synthesis: An easy technique for the positionally addressable, parallel chemical synthesis on a membrane support," Tetrahedron, vol. 48, pp. 9217-9232 (1992).
Fu, H. et al., "14-3-3 proteins: structure, function and regulation," Annul. Rev. Pharmacol. Toxicol., vol. 40, pp. 617-647 (2000).
Furst et al., "Consensus Statement: Updated consensus statement on biological agents, specifically tumour necrosis factor α (TNFα) blocking agents and interleukin-1 receptor antagonist (IL-1ra), for the treatment of rheumatic diseases, 2005" Ann. Rheum Dis., vol. 64, pp. iv2-iv14 (2005).

Ghahary, A, et al., "Keratinocyte-releasable stratifin functions as a potent collagenase-stimulating factor in fibroblasts," J. Invest. Dermatol., vol. 122, pp. 1188-1197 (2004).
Gilbert M. R., "Neurological Complications" in Abeloff MD et al., Clinical Oncology, 3rd Ed., pp. 1213-1246, Churchill Livingstone/ Elsevier Press, New York (2004).
Goldstein et al., "Selective p38α Inhibitors Clinically Evaluated for the Treatment of Chronic Inflammatory Disorders," J. Med. Chem., vol. 53, pp. 2345-2353 (2010).
Harris E D Jr., "Cytokines, Lymphokines, Growth Factors, and Chemokines," In: Rheumatoid Arthritis. Philadelphia: W.B. Saunders Company, pp. 105-125 (1997).
Harris E D Jr., "History and Epidemiology of Rheumatoid Arthritis: How long has it affected us, and who is at risk?," In: Rheumatoid Arthritis. Philadelphia: W.B. Saunders Company, pp. 121-127 (1997).
Harris E D Jr., "Introduction," In: Rheumatoid Arthritis. Philadelphia: W.B. Saunders Company, pp. xix-xxiii (1997).
Harris E D Jr., "Rheumatoid Synovium: Complex, and More Than the Sum of its Parts. In: Rheumatoid Arthritis," Philadelphia: W.B. Saunders Company, pp. 126-149, (1997).
Harlow, E., and Lane, D., "Antibodies: A Laboratory Manual," pp. 553-612, Cold Spring Harbor Laboratory Press, Cold Spring Harbor (1988).
Hermeking, H. et al., "14-3-3σ is a p53-regulated inhibitor of G2/M progression," Molecular Cell, vol. 1, pp. 3-11 (1997).
Hopp, Thomas P. and Woods, Kennith, R. et al., "Prediction of protein antigenic determinants from amino acid sequences," Proc. Natl. Acad. Sci. USA., vol. 78, No. 6, pp. 3824-3828 (1981).
Hsich, G, et al., "The 14-3-3 brain protein in cerebrospinal fluid as a marker for transmissible spongiform encephalopathies," N. Engl. J. Med., vol. 335, pp. 924-930 (1996).
14-3-3 etal Antibody (6A12) : sc-293464 https://www.scbt.com/ scbt/product/14-3-3-eta-antibody-6a12, downloaded Apr. 17, 2017, 4 pages total.
Ichimura, T. et al., "Brain 14-3-3 protein is an activator protein that activates tryptophan 5-monooxynease in the presence of $Ca^{2+}$, calmodulin-dependent protein kinase II," FEBS Lett., vol. 219, pp. 79-82 (1987).
Ichimura, T. et al., "Molecular cloning of cDNA coding for brain-specific 14-3-3 protein, a protein kinase-dependent activator of tyrosine and tryptophan hydroxylases," Proc. Natl. Acad. Sci. USA, vol. 85, pp. 7084-7088 (1988).
Jamal et al., "Increased expression of human type IIa secretory phospholipase A2 antigen in arthritic synovium," Ann. Rheum. Dis., vol. 57, pp. 550-558 (1998).
JaMBW Chapter 3.1.7, Antigenicity Plot (employing Hopp and Woods method), (http://www.bioinformatics.org/JaMBW/3/1/7/), pp. 1-2, printed Sep. 26, 2012.
Jasser, MZ et al., "Induction of stromelysin-1 and collagenase synthesis in fibrochondrocytes by tumor necrosis factor-alpha," Matrix Biology vol. 14, p. 241 (1994).
Jiang, J. et al., "Multifunctional proteins bridge mitosis with motility and cancer with inflammation and arthritis," The Scientific World Journal, vol. 10, pp. 1244-1257 (2010).
Kandpal et al., "Expression of Protein Kinase Regulator Genes in Human Ear and Cloning of a Gamma Subtype of the 14-3-3 Family of Proteins," DNA and Cell Biology, vol. 16(4), pp. 455-462 (1997).
Katrib, A. et al., "What can we learn from the synovium in early rheumatoid arthritis?," Inflamm. Res. vol. 51, pp. 170-175 (2002).
Katz, A. B. et al., "A Partial Catalog of Proteins Secreted by Epidermal Keratinocytes in Culture," J. Invest. Dermatol., vol. 112, pp. 818-821 (1999).
Kim et al., "When does rheumatoid arthritis begin and why do we need to know?," Arthritis. Reheum., vol. 43, pp. 473-484 (2000).
Kim et al., "Role of the 14-3-3η as a Positive Regulator of the Glucocorticoid Receptor Transcriptional Activation," Endocrinology, vol. 146(7), pp. 3133-3140 (2005).
Kohler et al., "Continuous cultures of fused cells secreting antibody of predefined specificity," Nature, vol. 256, pp. 495-497 (1975).
Konttinen et al., "New collagenolytic enzymes identified at the pannus-hard tissue junction in rheumatoid arthritis: destruction from above," Matrix Biol. Vo. 17(8-9), pp. 585-601 (1998).

(56) References Cited

OTHER PUBLICATIONS

Konttinen et al., "Analysis of 16 Different Matrix Metalloproteinases (MMP-1 to MMP-20) in The Synovial Membrane: different profiles in trauma and rheumatoid arthritis," Ann. Rheum. Dis., vol. 58, pp. 691-697 (1999).
Krensky et al., "Immunomodulators: Immunosuppressive Agents, Tolerogens, and Immunostimulants," in Hardman—10th Ed., pp. 1461-1483, McGraw Hill, New York (2001).
Laronga, C. et al., "Association of the cyclin-dependent kinases and 14-3-3 sigma negatively regulates cell cycle progression," J. Biol. Chem., vol. 275(30), pp. 23016-23112 (2000).
Leite, John—Invitrogen Corporation, Carlsbad, CA, USA, "Protein detection by Mass Spectrometry," www.invitrogen.com/piq., downloaded Jan. 4, 2013 , one page.
Lindy, O. et al., "Matrix metalloproteinase 13 (collagenase 3) in human rheumatoid synovium," Arthritis Rheum., vol. 40(8), pp. 1391-1399 (1997).
Lipsky, Peter E., "Rheumatoid Arthritis", in BRAUNWALD—Harrison's Principles of Internal Medicine, 15th Ed., pp. 1928-1937, McGraw Hill, New York (2001).
Ma et al., "Enhanced production of mouse hybridomas to picomoles of antigen using EL-4 conditioned media with an in vitro immunization protocol," In Vitro, vol. 20(9), p. 739-742 (1984).
Maksymowych et al., "Autoantibody to 14-3-3 ETA Is a Novel Biomarker Associated With MRI Inflammation and Radiographic Progression in Axial Spondyloarthritis," Ninth International Congress on Spondyloarthritis, Clinical and Experimental Rheumatology, vol. 32, pp. 765-838 (2014).
Maksymowych et al., "14-3-3η Autoantibodies: Diagnostic Use in Early Rheumatoid Arthritis," The Journal of Rheumatology, vol. 42, pp. 1-9 (2015).
Martin et al., "Antibodies against the major brain isoforms of 14-3-3 protein. An antibody specific for the Nacetylated amino-terminus of a protein," FEBS Letters, vol. 331(3), pp. 296-303 (1993).
Martin et al., "Subcellular Localisation of 14-3-3 Isoforms in Rat Brain Using Specific Antibodies," J. of Neurochemistry, vol. 63, pp. 2259-2265 (1994).
McInnes et al., "Cell-cell interactions in synovitis interactions between T lymphocytes and synovial cells," Arthritis Research, vol. 2(5), pp. 374-378 (2000).
Megidish et al., "A Novel Sphingosine-dependent Protein Kinas (SDK1) Specifically Phosphorylates Certain Isoforms of 14-3-3 Protein," J. Biol. Chem. vol. 273, No. 34, pp. 21834-21845 (1998).
Miranda-Carús, et al., "IL-15 and the initiation of cell contact-dependent synovial fibroblast-T lymphocyte cross-talk in rheumatoid arthritis: effect of methotrexate," J. Immunol., vol. 173, pp. 1463-1476 (2004).
Molina et al., "Improved Performances of Spot Multiple Peptide Synthesis," Journal of Peptide Application, Synthesis and Analysis, vol. 9, No. 3, pp. 151-155 (1996).
Moore et al., "Nutrition and Lysosomal Activity. The influence of vitamin E deficiency and its duration on the stability of lysosomes in the kidneys of rats," Biochem. J., vol. 103, pp. 923-928 (1967).
Moore et al., "Specific Acidic Proteins of the Nervous System", in Carson FD, pp. 343-359 (1967).
Neeck et al., "Involvement of the glucocorticoid receptor in the pathogenesis of rheumatoid arthritis," Ann. New York Academy of Sciences, vol. 966, pp. 491-495 (2002).
Pap, et al., "Differential expression pattern of membrane-type matrix metalloproteinases in rheumatoid arthritis," Arthritis Rheum., vol. 43(6), pp. 1226-1232 (2000).
Plotz, "The autoantibody repertoire: searching for order," Nat. Immunol. Rev., vol. 3, pp. 73-78 (2003).
Poole, A. R., "Cartilage in Health and Disease," in KOOPMAN WJ—Arthritis and Allied Conditions, 14th Ed., pp. 226-284, Williams & Wilkins, Baltimore (2001).
Roman-Blas, J. A. and Jimenez, S. A., "NF-κB as a potential therapeutic target in osteoarthritis and rheumatoid arthritis," Osteoarthritis and Cartilage, vol. 14, pp. 839-848 (2006).
Sakaguchi et al., "Animal models of arthritis caused by systemic alteration of the immune system," Curr. Opin. Immunol., vol. 17(6), pp. 589-594 (2005).
Sambrook, J., "Molecular Cloning—Protein Interaction Technologies—A Laboratory Manual," pp. 655-688, Cold Spring Harbor Laboratory Press (2001).
Santa Cruz Biotech, "14-3-3 eta Antibodies," downloaded Mar. 31, 2015, 2 pages.
Sato et al., "14-3-3η is a novel regulator of parkin ubiquitin ligase," The EMBO Journal, vol. 25, pp. 211-221 (2006).
Satoh et al., "The 14-3-3 protein ε isoform expressed in reactive astrocytes in demyelinating lesions of multiple sclerosis binds to vimentin and glial fibrillary acidic protein in culture human astrocytes," Amer. J. of Pathology, vol. 165, pp. 577-592 (2004).
Scheiman, James M and Fendrick, A Mark, "Practical approaches to minimizing gastrointestinal and cardiovascular safety concerns with COX-2 inhibitors and NSAIDs," Arth. Res and Therap. vol. 9, Suppl. 4, pp. S23-S29 (2005).
Sjowall et al., "Beware of Antibodies to Dietary Proteins in "Antigen-specific" Immunoassays! Falsely Positive Anticytokine Antibody Tests Due to Reactivity with Bovine Serum Albumin in Rheumatoid Arthritis (The Swedish TIRA Project)," J Rheumatol, vol. 38, pp. 215-220 (2011).
Skogh et al., "Twenty Eight Joint Count Disease Activity Score in Recent Onset Rheumatoid Arthritis Using C Reactive Protein . . . " Ann. Rheum Dis. vol. 62, pp. 681-682 (2003).
Smeets et al., "The effects of interferon-beta treatment of synovial inflammation and expression of metalloproteinases with rheumatoid arthritis," Arthritis Rheum., vol. 43, No. 2, pp. 270-274 (2000).
Sorsa et al., "Collagenase in synovitis of rheumatoid arthritis," Arthritis Rheum., vol. 22, pp. 44-53 (1992).
Takashashi et al., "Functional interaction of the immunosuppressant mizoribine with the 14-3-3 protein," Biochemical and Biophysical Research Communications, vol. 274, pp. 87-92 (2000).
Tohyama et al., "Localization of human glucocorticoid receptor in rheumatoid synovial tissue of the knee joint," Scandinavian J. Rheum., vol. 34, pp. 426-432 (2005).
Toker et al., "Protein kinase C inhibitor proteins. Purification from sheep brain and sequence similarity to lipocortins and 14-3-3 protein," Eur. J. Biochem., vol. 191(2), pp. 421-429 (1990).
Tolboom et al., "Invasive properties of fibroblast-like synoviocytes: correlation with growth characteristics and expression of MMP-1, MMP-3, and MMP-10," Ann. Rheum. Dis., vol. 61, pp. 975-980 (2002).
Ubl et al., "14-3-3 protein is a component of Lewy bodies in Parkinson's disease—Mutation analysis and association studies of 14-3-3 eta," Molecular Brain Research, vol. 108, pp. 33-39 (2002).
Umahara et al., "Intranuclear localization and isoform-dependent translocation of 14-3-3 proteins in human brain with infarction," J. Neurology Sciences, vol. 260, pp. 159-166 (2007).
Van Everbroeck et al., "14-3-3 y-isoform detection distinguishes sporadic Creutzfeldt-Jakob disease from other dementias," J. Neurology Neurosurgery and Psychiatry vol. 76, pp. 100-102 (2005).
Van Herwijnen et al., "Heat shock proteins can be targets of regulatory T cells for therapeutic intervention in rheumatoid arthritis," International Journal of Hyperthermia, vol. 29(5), pp. 448-454 (2013).
Vierboom et al., "Preclinical models of arthritic disease in non-human primates," Drug Discovery Today, vol. 12, pp. 327-335 (2007).
Vincent et al., "High diagnostic value in rheumatoid arthritis of antibodies to the stratum corneum of rat oesophagus epithelium, so-called 'antikeratin antibodies'," Ann. Rheum. Dis., vol. 48, pp. 712-722 (1989).
Wadhwa et al., "Neutralizing antibodies to granulocyte-macrophage colony-stimulating factor, interleukin-1α and interferon-α but not other cytokines in human immunoglobulin preparations," Immunology, vol. 99, pp. 113-123 (2000).
Wang et al., "Isolation of high-affinity peptide antagonists of 14-3-3 proteins by phage display," Biochemistry, vol. 38, pp. 12499-12504 (1999).
Wilker et al., "14-3-3 Proteins—a focus on cancer and human disease," J. Mo. Cell Cardiol., vol. 37(3), pp. 633-642 (2004).

(56) References Cited

OTHER PUBLICATIONS

Williams, Richard O., "Collagen-induced arthritis as a model for rheumatoid arthritis," Methods Mol. Med. vol. 98, pp. 207-216 (2004).
Xiao et al., "An approach to studying lung cancer-related proteins in human blood," Molecular & Cellular Proteomics, vol. 4, pp. 1480-1486 (2005).
Yaffe, Micahel B., "How do 14-3-3 proteins work?—Gatekeeper phosphorylation and the molecular anvil hypothesis," FEBS Lett., vol. 513(1), pp. 53-57 (2002).
Yamamura et al., "Effector function of resting T cells: activation of synovial fibroblasts," J. Immunol., vol. 166, pp. 2270-2275 (2001).
Yao et al., "Intra-articular injection of recombinant TRAIL induces synovial apoptosis and reduces inflammation in a rabbit knee model of arthritis," Arthritis Research and Therapy, vol. 8(1), pp. 1-8 (2006).
Moreira et al., "A Combined Proteome and Ultrastructural Localization Analysis of 14-3-3 Proteins in Transformed Human Amnion (AMA) Cells," Molecular & Cellular Proteomics, vol. 7, pp. 1225-1240 (2008).
R&D Systems 2007, "Affinity-Purified Goat Anti-human/mouse/rat 14-3-3 eta Antibody," Catalog No. AF4420 (2007).
Wakabayashi et al., "Increased concentrations of 14-3-3ε, γ and ζ isoforms in cerebrospinal fluid of AIDS patients with neuronal destruction," Clinica Chimica Acta, 312(1-2): pp. 97-105 (2001).
Qiu et al., "Occurrence of autoantibodies to annexin I, 14-3-3 theta and LAMR1 in prediagnostic lung cancer sera." Journal of Clinical Oncology, vol. 26, No. 31, pp. 5060-5066 (2008).
Goel et al., "Plasticity within the Antigen-Combining Site May Manifest as Molecular Mimicry in the Humoral Immune Response," J. Immunol. vol. 173, pp. 7358-7367 (2004).
Qi et al., "Isoform-Specific Expression of 14-3-3 Proteins in Human Lung cancer Tissues," Int. J. Cancer, vol. 113, pp. 359-363 (2005).

\* cited by examiner

```
                         SEQUENCE LISTING

<160> NUMBER OF SEQ ID NOS: 33

<210> SEQ ID NO 1
<211> LENGTH: 15
<212> TYPE: PRT
<213> ORGANISM: Homo sapiens

<400> SEQUENCE: 1

Leu Glu Thr Val Cys Asn Asp Val Leu Ser Leu Leu Asp Lys Phe
1               5                   10                  15

<210> SEQ ID NO 2
<211> LENGTH: 9
<212> TYPE: PRT
<213> ORGANISM: Homo sapiens

<400> SEQUENCE: 2

Glu Gln Ala Cys Leu Leu Ala Lys Gln
1               5

<210> SEQ ID NO 3
<211> LENGTH: 12
<212> TYPE: PRT
<213> ORGANISM: Homo sapiens

<400> SEQUENCE: 3

Asn Ser Val Val Glu Ala Ser Glu Ala Ala Tyr Lys
1               5                   10

<210> SEQ ID NO 4
<211> LENGTH: 9
<212> TYPE: PRT
<213> ORGANISM: Homo sapiens

<400> SEQUENCE: 4

Asn Ser Val Val Glu Ala Ser Glu Ala
1               5

<210> SEQ ID NO 5
<211> LENGTH: 9
<212> TYPE: PRT
<213> ORGANISM: Homo sapiens

<400> SEQUENCE: 5

Val Glu Ala Ser Glu Ala Ala Tyr Lys
1               5

<210> SEQ ID NO 6
<211> LENGTH: 8
<212> TYPE: PRT
<213> ORGANISM: Homo sapiens
```

```
<400> SEQUENCE: 6

Glu Gln Met Gln Pro Thr His Pro
1               5

<210> SEQ ID NO 7
<211> LENGTH: 10
<212> TYPE: PRT
<213> ORGANISM: Homo sapiens

<400> SEQUENCE: 7

Thr His Pro Ile Arg Leu Gly Leu Ala Leu
1               5                   10

<210> SEQ ID NO 8
<211> LENGTH: 11
<212> TYPE: PRT
<213> ORGANISM: Homo sapiens

<400> SEQUENCE: 8

Val Lys Ala Tyr Thr Glu Lys Ile Glu Lys Glu
1               5                   10

<210> SEQ ID NO 9
<211> LENGTH: 12
<212> TYPE: PRT
<213> ORGANISM: Homo sapiens

<400> SEQUENCE: 9

Gln Lys Thr Met Ala Asp Gly Asn Glu Lys Lys Leu
1               5                   10

<210> SEQ ID NO 10
<211> LENGTH: 9
<212> TYPE: PRT
<213> ORGANISM: Homo sapiens

<400> SEQUENCE: 10

Ala Ser Gly Glu Lys Lys Asn Ser Val
1               5

<210> SEQ ID NO 11
<211> LENGTH: 9
<212> TYPE: PRT
<213> ORGANISM: Homo sapiens

<400> SEQUENCE: 11

Lys Thr Met Ala Asp Gly Asn Glu Lys
1               5

<210> SEQ ID NO 12
<211> LENGTH: 9
<212> TYPE: PRT
<213> ORGANISM: Homo sapiens

<400> SEQUENCE: 12

Glu Leu Asn Glu Pro Leu Ser Asn Glu
1               5

<210> SEQ ID NO 13
<211> LENGTH: 15
<212> TYPE: PRT
<213> ORGANISM: Homo sapiens
```

<400> SEQUENCE: 13

Leu Leu Asp Lys Phe Leu Ile Lys Asn Cys Asn Asp Phe Gln Tyr
1               5                   10                  15

<210> SEQ ID NO 14
<211> LENGTH: 14
<212> TYPE: PRT
<213> ORGANISM: Homo sapiens

<400> SEQUENCE: 14

Tyr Tyr Arg Tyr Leu Ala Glu Val Ala Ser Gly Glu Lys Lys
1               5                   10

<210> SEQ ID NO 15
<211> LENGTH: 11
<212> TYPE: PRT
<213> ORGANISM: Homo sapiens

<400> SEQUENCE: 15

Tyr Glu Ile Gln Asn Ala Pro Glu Gln Ala Cys
1               5                   10

<210> SEQ ID NO 16
<211> LENGTH: 13
<212> TYPE: PRT
<213> ORGANISM: Homo sapiens

<400> SEQUENCE: 16

Ala Glu Leu Asp Thr Leu Asn Glu Asp Ser Tyr Lys Asp
1               5                   10

<210> SEQ ID NO 17
<211> LENGTH: 14
<212> TYPE: PRT
<213> ORGANISM: Homo sapiens

<400> SEQUENCE: 17

Leu Leu Ser Val Ala Tyr Lys Asn Val Val Gly Ala Arg Arg
1               5                   10

<210> SEQ ID NO 18
<211> LENGTH: 9
<212> TYPE: PRT
<213> ORGANISM: Homo sapeins

<400> SEQUENCE: 18

Glu Gln Ala Glu Arg Tyr Asp Asp Met
1               5

<210> SEQ ID NO 19
<211> LENGTH: 9
<212> TYPE: PRT
<213> ORGANISM: Homo sapiens

<400> SEQUENCE: 19

Tyr Tyr Arg Tyr Leu Ala Glu Val Ala
1               5

<210> SEQ ID NO 20
<211> LENGTH: 8
<212> TYPE: PRT
<213> ORGANISM: Homo sapiens

```
<400> SEQUENCE: 20

Glu Ser Lys Val Phe Tyr Leu Lys
1               5

<210> SEQ ID NO 21
<211> LENGTH: 9
<212> TYPE: PRT
<213> ORGANISM: Homo sapiens

<400> SEQUENCE: 21

Thr Leu Asn Glu Asp Ser Tyr Lys Asp
1               5

<210> SEQ ID NO 22
<211> LENGTH: 8
<212> TYPE: PRT
<213> ORGANISM: Homo sapiens

<400> SEQUENCE: 22

Lys Lys Leu Glu Lys Val Lys Ala
1               5

<210> SEQ ID NO 23
<211> LENGTH: 11
<212> TYPE: PRT
<213> ORGANISM: Homo sapiens

<400> SEQUENCE: 23

Glu Lys Lys Leu Arg Lys Val Lys Ala Tyr Arg
1               5                   10

<210> SEQ ID NO 24
<211> LENGTH: 17
<212> TYPE: PRT
<213> ORGANISM: Homo sapiens

<400> SEQUENCE: 24

Lys Lys Asn Ser Val Val Glu Ala Ser Glu Ala Ala Tyr Lys Glu Ala Phe
1               5                   10                  15

<210> SEQ ID NO 25
<211> LENGTH: 16
<212> TYPE: PRT
<213> ORGANISM: Homo sapiens

<400> SEQUENCE: 25

Asp Lys Phe Leu Ile Lys Asn Cys Asn Asp Phe Gln Tyr Glu Ser Lys
1               5                   10                  15

<210> SEQ ID NO 26
<211> LENGTH: 10
<212> TYPE: PRT
<213> ORGANISM: Homo sapiens

<400> SEQUENCE: 26

Gln Gln Asp Glu Glu Ala Gly Glu Gly Asn
1               5                   10

<210> SEQ ID NO 27
<211> LENGTH: 9
<212> TYPE: PRT
<213> ORGANISM: Homo sapiens
```

```
<400> SEQUENCE: 27

Asn Glu Lys Lys Leu Glu Lys Val Lys
1               5

<210> SEQ ID NO 28
<211> LENGTH: 13
<212> TYPE: PRT
<213> ORGANISM: Homo sapiens

<400> SEQUENCE: 28

Leu Asp Lys Phe Leu Ile Lys Asn Cys Asn Asp Phe Gln
1               5                   10

<210> SEQ ID NO 29
<211> LENGTH: 6
<212> TYPE: PRT
<213> ORGANISM: Homo sapiens

<400> SEQUENCE: 29

Glu Lys Lys Asn Ser Val
1               5

<210> SEQ ID NO 30
<211> LENGTH: 13
<212> TYPE: PRT
<213> ORGANISM: Homo sapiens

<400> SEQUENCE: 30

Leu Asp Lys Phe Leu Ile Lys Asn Ser Cys Asn Asp Phe
1               5                   10

<210> SEQ ID NO 31
<211> LENGTH: 10
<212> TYPE: PRT
<213> ORGANISM: Homo sapiens

<400> SEQUENCE: 31

Lys Lys Leu Glu Lys Val Lys Ala Tyr Arg
1               5                   10

<210> SEQ ID NO 32
<211> LENGTH: 15
<212> TYPE: PRT
<213> ORGANISM: Homo sapiens

<400> SEQUENCE: 32

Lys Asn Ser Val Val Glu Ala Ser Glu Ala Ala Tyr Lys Glu Ala
1               5                   10                  15

<210> SEQ ID NO 33
<211> LENGTH: 12
<212> TYPE: PRT
<213> ORGANISM: Homo sapiens

<400> SEQUENCE: 33

Asp Arg Glu Gln Leu Leu Gln Arg Ala Arg Leu Ala
1               5                   10
```

COMPOSITIONS AND METHODS FOR CHARACTERIZING ARTHRITIC CONDITIONS

FIELD

Described herein are autoantibodies to 14-3-3 and methods of using the same to evaluate arthritic conditions.

BACKGROUND

Arthritis, or arthralgia, generally refers to inflammatory disorders of the joints of the body, and is usually accompanied by pain, swelling and stiffness. Arthritis may result from any of several causes including infection, trauma, degenerative disorders, metabolic disorders or disturbances or other unknown etiologies. Osteoarthritis (OA) is a common form of non-inflammatory arthritis that may occur following trauma to a joint, following an infection of a joint or simply as a result of aging. Osteoarthritis is also known as degenerative joint disease. Rheumatoid arthritis (RA) is traditionally considered a chronic, inflammatory autoimmune disorder that causes the immune system to attack the joints. It is a disabling and painful inflammatory condition which can lead to substantial loss of mobility due to pain and joint destruction. Ankylosing spondylitis (AS) is a chronic, painful, degenerative inflammatory arthritis primarily affecting the spine and sacroiliac joints, causing eventual fusion of the spine.

The body's articulating joints are called synovial joints, and each synovial joint generally comprises the opposing ends of two adjacent bones. The ends of the bones are encased in cartilage tissue while the entire joint area is encased in a protective soft tissue called synovium which comprises synovial membrane. The synovial membrane produces and releases a lubricating synovial fluid into cavities within the joint. In normal joints, the volume of synovial fluid is quite small. In addition to its lubricating function, synovial fluid also acts as a reservoir for solutes and a few resting mononuclear and synovial cells.

The synovium can become irritated and thickened in response to many insults believed to promote arthritis, including trauma to the joint and/or malfunction of the body's immune system. The consequences of such insults include excessive production and release of synovial fluid into the joint, thereby causing swelling within and about the joint area. The increased volumes are typically accompanied by increased concentrations in the synovial fluid of fibroblast-like synoviocyte cells (FLS cells), pro-inflammatory cytokines such as interleukin-1 (IL-1) and tumor necrosis factor (TNF-alpha), histamine proteins and peptides, and degradative enzymes such as matrix metalloproteases (MMPs). The FLS cells comprise about two-thirds of the synovial cells in normal synovial fluid, have well-defined secretory systems, and under conditions of trauma or inflammation commonly secrete large amounts of MMPs into the synovial fluid, specifically MMP-1, 3, 8, 9, 10, 11 and 13. MMP-1 and MMP-3 are considered to have significant roles in the progressive structural damage of cartilage and underlying bone tissues comprising joints. Known factors that activate FLS cells to produce MMP-1 and MMP-3 include IL-1 and TNF-alpha.

The causative agents for RA, AS and OA are currently not well-defined. However, the physiological events associated with progression of the disease, from prolonged periods of swelling and inflammation caused by excessive synovial fluid accumulation in the joints, through degradation and deterioration of the cartilage and underlying bone tissues by degradative enzyme activities, and the accompanying FLS cell proliferation into bone which results in permanent structural damage, are known. If detected early enough, the potential long-term deleterious effects of disease can be reversed, or at least minimized, with appropriate physical and medical therapies. Accordingly, considerable efforts have been placed on the identification of suitable biomarkers for early identification of arthritis. To this end, Kilani et al. (2007, J. Rheum. 34: 1650-1657; WO 2007/128132) have reported that two members of the 14-3-3 protein family, particularly 14-3-3 eta and 14-3-3 gamma, are present within the synovial fluid and serum of patients with arthritis, and these isoforms are directly correlated with the levels of MMP-1 and MMP-3 in the synovial fluid and serum.

SUMMARY

The present invention concerns the finding that the presence of autoantibodies directed against 14-3-3 protein(s) in biological samples correlates with diagnosis and/or prognosis of an arthritic condition. The strong correlation between such autoantibodies and an arthritic condition allows for diagnosis and/or prognosis of the arthritic condition by assaying for autoantibodies against, or circulating immune complexes with at least one 14-3-3 protein or a fragment thereof in a biological sample from a subject. In preferred embodiments, the 14-3-3 protein(s) comprise the eta and/or gamma isoforms.

Accordingly, described herein are methods for evaluating and/or characterizing an arthritic condition in a mammalian subject comprising contacting a biological sample from the subject with at least one 14-3-3 protein or fragment thereof and detecting an autoantibody against the 14-3-3 protein or fragment thereof, wherein the presence/quantity of an autoantibody against said at least one 14-3-3 protein or fragment thereof is indicative of the existence and/or status of the arthritic condition in the subject. Also provided herein are methods for evaluating and/or characterizing an arthritic condition in a mammalian subject comprising detecting circulating immune complexes between an autoantibody and at least one 14-3-3 protein in a biological sample from the subject, wherein the presence/quantity of existing immune complexes in the sample is indicative of the existence and/or status of the arthritic condition in the subject.

The 14-3-3 protein or fragment thereof may comprise an epitope shared between a plurality of 14-3-3 protein isoforms, or may comprise an epitope unique to one or a subset of 14-3-3 protein isoforms. In preferred embodiments, the 14-3-3 protein or fragment thereof comprises a 14-3-3 eta and/or gamma epitope. In one embodiment, the 14-3-3 protein of fragment thereof comprises a 14-3-3 eta epitope shared by at least one other 14-3-3 isoform, e.g. 14-3-3 gamma. In another embodiment, the 14-3-3 eta epitope is unique to 14-3-3 eta.

In one embodiment, the detecting step includes quantifying/measuring the level of autoantibodies against, or immune complexes with, 14-3-3 protein or a fragment thereof in the biological sample for comparison with a control sample. Accordingly, the presently-claimed methods for evaluating an arthritic condition in a subject may provide prognostic as well as diagnostic determinations.

In one aspect, the control sample is a normal control, and the comparison is indicative of an arthritis diagnosis. In one embodiment, an increased level of autoantibody against, or immune complexes with, 14-3-3 protein or a fragment thereof in said biological sample in comparison with a normal control sample (e.g., from another subject not having an arthritic condition) is a diagnostic indicator of an arthritic condition in said subject.

Accordingly, in some embodiments, the presence of autoantibodies to 14-3-3 protein or immune complexes thereof in the biological sample from the subject and/or the presence of an increased level of such autoantibodies or immune complexes in the biological sample from the subject relative to a level of such autoantibodies or immune complexes in a normal (i.e. non-arthritic) control sample provides a diagnosis that the subject has an arthritic condition.

In one aspect, the control sample is a previous biological sample from the mammalian subject, and the comparison is indicative of disease progression and/or efficacy of a therapeutic regimen. In one embodiment, a decreased level of autoantibodies to 14-3-3 or circulating immune complexes thereof in said sample compared to the previous sample (e.g., a baseline biological sample from said subject) is indicative of the efficacy of an ongoing therapeutic regimen.

Accordingly, in some embodiments, the relative level of autoantibodies against, or immune complexes with, 14-3-3 or a fragment thereof detected in the biological sample from the subject compared to the level of such autoantibodies or complexes present in a baseline biological sample from the same subject provides a prognosis of the arthritic condition, or is indicative of the efficacy of a therapeutic regimen.

In one aspect, the control sample is an arthritic control, and the comparison is indicative of disease prognosis. In one embodiment, the relative level of autoantibodies to 14-3-3 or immune complexes thereof in comparison to an arthritic control sample (e.g., from another subject with a well-defined arthritic condition) is a prognostic indicator of arthritis.

Accordingly, in some embodiments, subjects with different arthritic status have detectable differences in levels of autoantibodies to at least one 14-3-3 protein or fragment thereof, and/or circulating immune complexes of such, and these differences are of prognostic relevance. In one example, disclosed herein are methods that may be used to determine a specific disease stage or the histopathological phenotype of an arthritic condition based on the relative level of autoantibody detected in a subject compared to levels previously determined to exist throughout the course of the arthritic condition, e.g., before treatment, during treatment, after treatment, in another patient, etc. In another example, the methods disclosed herein may be used to classify a biological sample as being from a subject at high risk for manifestation of an arthritic condition based on the relative level of autoantibodies detected in the biological sample compared to a control sample, which may be, e.g., stored in a database.

In another aspect, the methods disclosed herein may be used to predict the responsiveness of a subject to a therapeutic regimen based on the relative level of autoantibodies detected in a biological sample from the subject compared to a control sample, e.g., of a second biological sample from a second subject that was successfully treated with the therapeutic regimen.

Accordingly, in some embodiments, the relative level of autoantibodies against, or immune complexes with, at least one 14-3-3 protein or fragment thereof in the biological sample from the first subject is compared to the level of autoantibodies against, or immune complexes with, 14-3-3 in biological samples from subjects whose abilities to respond to a treatment are known, wherein such comparison determines the response potential of the first subject to the treatment. Determination of the sensitivity of the subject to a therapeutic regimen may then be used to inform methods of treating a subject with an arthritic condition. For example, described herein are methods of treating a subject with an arthritic condition comprising measuring the level of autoantibody against 14-3-3 in a biological sample from the subject (e.g., by measuring the level of autoantibody/14-3-3 immune complex formation), correlating the level of autoantibody against or immune complex with 14-3-3 with sensitivity of the subject to a therapeutic regimen, and providing the therapeutic regimen to the subject. In one aspect, the invention provides methods for monitoring treatment of an arthritic condition, comprising determining the level of autoantibodies against, or immune complexes with, at least one 14-3-3 protein or fragment thereof in patient samples and monitoring the level of autoantibodies/immune complexes involving 14-3-3 in a patient undergoing treatment.

In another aspect, provided herein are methods for determining and/or differentiating the subtypes of arthritis in a patient. In this aspect, the relative level of autoantibodies against, or immune complexes with, at least one 14-3-3 protein or fragment thereof in the biological sample from the first subject is compared to the level of autoantibodies against, or immune complexes with, 14-3-3 in biological samples from one or more other subjects whose subtype of arthritis is known and/or previously-established, wherein such comparison determines the subtype of arthritis for the first subject.

Determination that that the levels of autoantibodies against, or immune complexes with, at least one 14-3-3 protein or fragment thereof in the biological sample from the first subject are similar to the levels of autoantibodies against, or immune complexes with, at least one 14-3-3 protein or fragment thereof in the biological sample from in the biological sample of an other subject whose subtype of arthritis is known and/or previously-established may indicate that the first subject has the same subtype of arthritis as the other subject. For example, similar levels of autoantibodies against, or immune complexes with, at least one 14-3-3 protein or fragment thereof in the biological sample from the first subject and in the biological sample of another subject known to have inflammatory arthritis, e.g., Rheumatoid arthritis, may determine that the first subject also has inflammatory arthritis, e.g., Rheumatoid arthritis.

Additionally, determination that that the levels of autoantibodies against, or immune complexes with, at least one 14-3-3 protein or fragment thereof in the biological sample from the first subject are dissimilar to the levels of autoantibodies against, or immune complexes with, at least one 14-3-3 protein or fragment thereof in the biological sample from in the biological sample of an other subject whose subtype of arthritis is known and/or previously-established may indicate that the first subject has a subtype of arthritis different than that of the other subject. For example, dissimilar levels of autoantibodies against, or immune complexes with, at least one 14-3-3 protein or fragment thereof in the biological sample from the first subject and in the biological sample of an other subject known to have non-inflammatory arthritis, e.g., osteoarthritis, may determine that the first subject has an inflammatory arthritis, e.g., Rheumatoid arthritis.

In one embodiment, the detecting step comprises an immunological-based technique, e.g., immunoprecipitation, ELISA, Western blot analysis, immunohistochemistry, immunofluorescence, "sandwich" immunoassays, immunoradiometric assays, gel diffusion precipitation reactions, immunodiffusion assays, in situ immunoassays, precipitation reactions, agglutination assays, complement fixation assays, protein A assays, immunoelectrophoresis assays, fluorescence activated cell sorting (FACS) analysis, radioimmunoassay, and the like.

Detecting and/or measuring autoantibodies against a 14-3-3 protein or fragment thereof according to the methods described herein may thus be performed by observing the formation of an immune complex between the autoantibody and 14-3-3 or fragment thereof in a sample, or alternatively determining the presence of an existing autoantibody/14-3-3 complex in a sample. In one embodiment, the formation may be detected by way of detectably labeled 14-3-3 protein(s) or fragment(s) thereof. In another embodiment, the complex may be detected by forming a second immune complex between the autoantibody/14-3-3 complex and a detectably labeled secondary antibody that binds immunoglobulin, e.g., the immunoglobulin backbone of the autoantibody.

In one embodiment, the methods involve detecting autoantibodies against 14-3-3 or circulating immune complexes thereof in the blood, synovial fluid, plasma, serum, or tissue (e.g. synovial joint, damaged joint tissue, etc.) of a patient. In one embodiment, detection is done by immunoprecipitation of autoantibodies against 14-3-3 from blood, synovial fluid, plasma, serum or tissue using 14-3-3 protein or fragment thereof. In one embodiment, detection involves the use of ELISA. In one embodiment, detection involves Western blot analysis of a sample comprising synovial fluid, plasma, or serum from a patient. In one embodiment, detection involves the use of radioimmunoassay. In one embodiment, detection involves the use of a strip test. In one embodiment, detection involves the use of a point of care test. In one embodiment, detection of autoantibodies against 14-3-3 or circulating complexes thereof is combined with detection of another marker of arthritis (e.g., MMP, anti-CCP, anti-RF and/or CRP).

Also described herein are kits comprising a reagent for evaluating an arthritic condition in a subject, wherein the reagent specifically recognizes autoantibodies to 14-3-3 protein or a fragment thereof. In one embodiment, the reagent may include a detectably labeled 14-3-3 protein or fragment thereof, which may also be immobilized on a solid support. The 14-3-3 protein or fragment thereof may comprise an epitope shared between a plurality of 14-3-3 protein isoforms, or may comprise an epitope unique to one or a subset of 14-3-3 protein isoforms. In preferred embodiments, the 14-3-3 protein or fragment thereof comprises a 14-3-3 eta and/or gamma epitope. In one embodiment, the 14-3-3 protein or fragment thereof comprises a 14-3-3 eta epitope shared by at least one other 14-3-3 isoform, e.g. 14-3-3 gamma. In another embodiment, the 14-3-3 eta epitope is unique to 14-3-3 eta.

DETAILED DESCRIPTION

Figure 1:
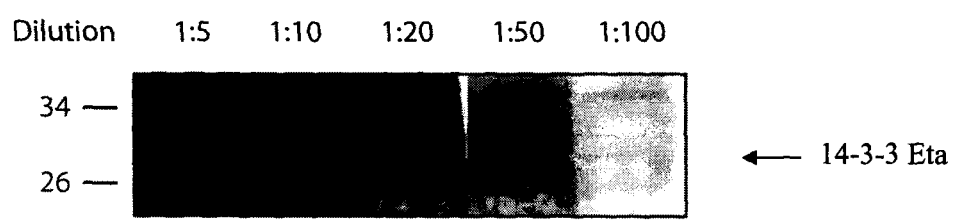
FIG. 1 shows a western blot of recombinant 14-3-3 Eta using serial dilution of serum from a patient diagnosed with rheumatoid arthritis (Sample 3323).

"Subject" and "patient" are used interchangeably and refer to, except where indicated, mammals such as humans and non-human primates, as well as rabbits, rats, mice, goats, pigs, and other mammalian species.

"Arthritic condition," "arthritis," and "arthralgia" are used interchangeably, and generally refer to, except where indicated, an inflammatory disorder of the joints of the body. Pain, swelling, stiffness, and difficulty of movement are frequently associated with arthritic conditions. Arthritis consists of more than 100 different conditions. These can be anything from relatively mild forms to crippling systemic forms, see, e.g., www.arthritis.ca/types%20of%20arthritis/default.asp?s=1. An arthritic condition may result from any of several causes, including infection, trauma, degenerative disorders, metabolic disorders or disturbances, or other unknown etiologies. An arthritic condition may be more specifically described according to the subtype, for example, rheumatoid arthritis, mixed connective tissue disease (MCTD), crystal induced arthritis, reactive arthritis, spondylarthropathy, osteoarthritis, sarcoidosis, palindromic rheumatism, post traumatic arthritis, malignancy related arthritis, septic arthritis, lyme arthritis, osteoarthritis, bacterial, infectious arthritis, etc. Arthritis may further accompany other identified disorders, including gout, ankylosing spondylitis, systemic lupus erythematosus, inflammatory bowel disease, psoriasis, etc. Well-defined arthritic condition refers to knowledge regarding the type of arthritis and its stage, e.g., onset, remission, relapse etc.

"Autoantibodies" are endogenous antibodies that specifically bind self antigens, i.e., a normal tissue component. An autoantibody is produced in response to a naturally occurring antigen of the same body that produces the autoantibody.

"Immunological binding" and "formation of an immune complex" are used interchangeably and as used in this context, generally refer to the non-covalent interactions of the type which occur between an antibody, e.g., an autoantibody, and an antigen for which the antibody is specific. The strength, or affinity of immunological binding interactions can be expressed in terms of the dissociation constant ($K_d$) of the interaction, wherein a smaller $K_d$ represents a greater affinity. Immunological binding properties can be quantified using methods well known in the art. For example, see Davies et al. (1990) Annual Rev. Biochem. 59:439-473. An antibody, or antigen-binding fragment thereof, is said to "specifically bind," "immunologically bind," and/or is "immunologically reactive" if it reacts at a detectable level (within, for example, an ELISA assay) with ligand, and does not react detectably with unrelated ligands under similar conditions.

"Antibody" refers to a composition comprising a protein that binds specifically to a corresponding antigen and has a common, general structure of immunoglobulins. The term antibody specifically covers polyclonal antibodies, monoclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. Typically, an antibody will comprise at least two heavy chains and two light chains interconnected by disulfide bonds, which when combined form a binding domain that interacts with an antigen. Each heavy chain is comprised of a heavy chain variable region (VH) and a heavy chain constant region (CH). The heavy chain constant region is comprised of three domains, CH1, CH2 and CH3, and may be of the mu, delta, gamma, alpha or epsilon isotype. Similarly, the light chain is comprised of a light chain variable region (VL) and a light chain constant region (CL). The light chain constant region is comprised of one domain, CL, which may be of the kappa or lambda isotype. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The heavy chain constant region mediates binding of the immunoglobulin to host tissue or host factors, particularly through cellular receptors such as the Fc receptors (e.g., FcγRI, FcγRII, FcγRIII, etc.). As used herein, antibody also includes an antigen binding portion of an immunoglobulin that retains the ability to bind antigen. These include, as examples, F(ab), a monovalent fragment of VL CL and VH CH antibody domains; and F(ab')$_2$ fragment, a bivalent fragment comprising two Fab fragments linked by a disulfide bridge at the hinge region. The term antibody also refers to recombinant single chain Fv fragments (scFv) and bispecific molecules such as, e.g., diabodies, triabodies, and tetrabodies (see, e.g., U.S. Pat. No. 5,844,094).

"Antigen" is to be construed broadly and refers to any molecule, composition, or particle that can bind specifically to an antibody. An antigen may have one or more epitopes that interact with the antibody, although it does not necessarily induce production of that antibody.

Accordingly, the terms "autoantibodies against 14-3-3" and "autoantibodies to 14-3-3" are used interchangeably and refer to endogenous antibodies produced by a mammalian subject that specifically bind a 14-3-3 protein or a fragment thereof from said host.

"14-3-3" and "14-3-3 protein" are used interchangeably and refer to at least one member of the 14-3-3 family of conserved intracellular regulatory molecules that are ubiquitously expressed in eukaryotes. 14-3-3 proteins have the ability to bind a multitude of functionally diverse signaling proteins, including kinases, phosphatases, and transmembrane receptors. Indeed, more than 100 signaling proteins have been reported as 14-3-3 ligands. 14-3-3 proteins may be considered evolved members of the Tetratrico Peptide Repeat superfamily. They generally have 9 or 10 alpha helices, and usually form homo- and/or hetero-dimer interactions along their amino-termini helices. These proteins contain a number of known domains, including regions for divalent cation interaction, phosphorylation & acetylation, and proteolytic cleavage, among others. There are seven distinct genetically encoded isoforms of the 14-3-3 proteins that are known to be expressed in mammals, with each isoform comprising between 242-255 amino acids. The seven 14-3-3 protein isoforms are designated as 14-3-3α/β (alpha/beta), 14-3-3δ/ξ (delta/zeta), 14-3-3ε (epsilon), 14-3-3γ (gamma), 14-3-3η (eta), 14-3-3τ/θ (tau/theta), and 14-3-3σ (sigma/stratifin). 14-3-3 proteins have a high degree of sequence similarity, and are known to undergo post-translational processing, e.g., phosphorylation, citrullination, etc. See, e.g., Megidish et al. (1998) *J. Biol. Chem.* 273: 21834-45. Consequently, anti-14-3-3 autoantibodies may specifically bind to and/or recognize more than one 14-3-3 protein isoform, or may specifically bind and/or recognize only one isoform (e.g., 14-3-3 eta). Additionally, anti-14-3-3 antibodies may bind to and/or recognize a 14-3-3-protein that has been modified, e.g., by natural (e.g., post-translational) or chemical processes.

The terms "specific binding" or "specifically binding" when used in reference to the interaction of an antibody and a protein or peptide means that the interaction is dependent upon the presence of a particular structure (i.e. epitope) on the protein; in other words the antibody is recognizing and binding to a specific protein structure rather than to proteins in general.

Epitopes are chemical features generally present on surfaces of molecules and accessible to interaction with an antibody. Typical chemical features are amino acids and sugar moieties, having three-dimensional structural characteristics as well as chemical properties including charge, hydrophilicity, and lipophilicity. Conformational epitopes are distinguished from non-conformational epitopes by loss of reactivity with an antibody following a change in the spatial elements of the molecule without any change in the underlying chemical structure. Accordingly, the term "epitope" when used in reference to 14-3-3 proteins or specific isomers generally refers to a determinant of the protein, including a modified 14-3-3 protein, that is capable of binding to an antibody, e.g., an autoantibody. Described herein are 14-3-3 epitopes that are recognized by autoantibodies in a patient diagnosed with arthritis, particularly Rheumatoid arthritis, methods of using such epitopes to evaluate and/or characterize an arthritic condition in a subject, and kits comprising such epitopes.

The 14-3-3 protein or fragment thereof may comprise an epitope shared between a plurality of 14-3-3 protein isoforms, or may comprise an epitope unique to one or a subset of 14-3-3 protein isoforms. "Shared" as used herein refers to a fragment or epitope in common between two or more 14-3-3 protein isoforms. In preferred embodiments, the 14-3-3 protein or fragment thereof comprises a 14-3-3 eta and/or gamma epitope. In one embodiment, the 14-3-3 protein of fragment thereof comprises a 14-3-3 eta epitope shared by at least one other 14-3-3 isoform, e.g. 14-3-3 gamma. In another embodiment, the 14-3-3 eta epitope is unique to 14-3-3 eta. Commonly recognized epitopes to 14-3-3 eta are included in Table 1 below.

TABLE 1

| 14-3-3 Eta epitopes | | |
|---|---|---|
| SEQ ID NO: 1 | 93-107 helix | LETVCNDVLSLLDKF |
| SEQ ID NO: 2 | 191-199 helix | EQACLLAKQ |
| SEQ ID NO: 3 | 144-155 helix | NSVVEASEAAYK |
| SEQ ID NO: 4 | 144-152 helix | NSVVEASEA |
| SEQ ID NO: 5 | 147-155 helix | VEASEAAYK |
| SEQ ID NO: 6 | 163-170 helix | EQMQPTHP |
| SEQ ID NO: 7 | 168-177 helix | THPIRLGLAL |
| SEQ ID NO: 8 | 82-92 helix | VKAYTEKIEKE |
| SEQ ID NO: 9 | 68-79 helix | QKTMADGNEKKL |
| SEQ ID NO: 10 | 138-146 helix | ASGEKKNSV |
| SEQ ID NO: 11 | 69-77 loop | KTMADGNEK |
| SEQ ID NO: 12 | 32-40 loop | ELNEPLSNE |

TABLE 1-continued 14-3-3 Eta epitopes

| SEQ ID NO: 13 | 103-117 | loop | LLDKFLIKNCNDFQY |
|---|---|---|---|
| SEQ ID NO: 14 | 130-143 | loop | YYRYLAEVASGEKK |
| SEQ ID NO: 15 | 184-194 | loop | YEIQNAPEQAC |
| SEQ ID NO: 16 | 206-218 | loop | AELDTLNEDSYKD |
| SEQ ID NO: 17 | 44-57 | non-helix | LLSVAYKNVVGARR |
| SEQ ID NO: 18 | 15-23 | non-helix | EQAERYDDM |
| SEQ ID NO: 19 | 130-138 | non-helix | YYRYLAEVA |
| SEQ ID NO: 20 | 118-125 | non-helix | ESKVFYLK |
| SEQ ID NO: 21 | 210-218 | non-helix | TLNEDSYKD |
| SEQ ID NO: 22 | 77-84 | non-helix | KKLEKVKA |
| SEQ ID NO: 23 | 76-86 | non-helix | EKKLRKVKAYR |
| SEQ ID NO: 24 | 142-158 | non-helix | KKNSVVEASEAAYKEAF |
| SEQ ID NO: 25 | 105-120 | non-helix | DKFLIKNCNDFQYESK |
| SEQ ID NO: 26 | 237-246 | non-helix | QQDEEAGEGN |
| SEQ ID NO: 27 | 75-82 | non-helix | NEKKLEKVK |
| SEQ ID NO: 28 | 104-116 | non-helix | LDKFLIKNCNDFQ |
| SEQ ID NO: 29 | 141-146 | non-helix | EKKNSV |
| SEQ ID NO: 30 | 104-115 | non-helix | LDKFLIKNCNDF |
| SEQ ID NO: 31 | 77-86 | non-helix | KKLEKVKAYR |
| SEQ ID NO: 32 | 143-157 | non-helix | KNSVVEASEAAYKEA |
| SEQ ID NO: 33 | 1-12 | non-helix | DREQLLQRARLA |

Diagnostic, Prognostic and Therapeutic Methods, and Treatment Monitoring

In one aspect, the invention provides methods for diagnosing diseases and conditions that involve autoantibodies against 14-3-3. In general, the presence or absence of an arthritic condition, or patient prognosis, may be determined by (a) contacting a biological sample obtained from a mammalian subject with at least one 14-3-3 protein or fragment thereof; (b) detecting in the sample the level of autoantibodies that specifically bind to the 14-3-3 protein or fragment thereof; and (c) comparing the level in such antibodies with an appropriate control.

The methods comprise using at least one 14-3-3 protein or fragment thereof to detect autoantibodies against the protein. There are a variety of assay formats known to those of ordinary skill in the art for using a protein to detect antibodies in a sample. See, e.g., Harlow and Lane, Antibodies: A Laboratory Manual, Cold Spring Harbor Laboratory, 1988. As nonlimiting examples, detection of autoantibodies against 14-3-3 may be performed using well-known methods or assays, e.g. immunoprecipitation, ELISA, Western blot analysis, immunohistochemistry, immunofluorescence, "sandwich" immunoassays, immunoradiometric assays, gel diffusion precipitation reactions, immunodiffusion assays, in situ immunoassays, precipitation reactions, agglutination assays, complement fixation assays, protein A assays, immunoelectrophoresis assays, fluorescence activated cell sorting (FACS) analysis, radioimmunoassay, a strip test, a point of care test, and the like. The ordinarily skilled artisan will recognize that these methods may also be used to measure the level of autoantibodies against, or immune complexes with, 14-3-3 proteins in the biological sample.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to arthritic conditions is utilized, including 14-3-3 proteins.

In one embodiment, the assays involve the use of at least one 14-3-3 protein or a fragment thereof immobilized on a solid support to bind to and capture autoantibodies that specifically bind the 14-3-3 protein(s) from the remainder of the sample. The bound autoantibodies may then be detected using a detection reagent that contains a reporter group and specifically binds to the antibody/protein complex. Such detection reagents may comprise, for example, a binding agent that specifically binds to the autoantibody such as an anti-human antibody.

The solid support may be any material known to those of ordinary skill in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The 14-3-3 protein or fragment thereof may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antibody and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and about 1 day. In one embodiment, a microtitre plate coated with streptavidin is used in conjunction with a biotinylated 14-3-3 protein or fragment thereof.

Covalent attachment of the 14-3-3 protein or fragment thereof to a solid support may generally be achieved by first reacting the support with a bifunctional reagent that will react with both the support and the 14-3-3 protein or fragment thereof. The captured autoantibody can then be detected using the non-competitive "sandwich" technique where labeled ligand for the autoantibody is exposed to the washed solid phase. Alternatively, competitive formats rely on the prior introduction of a labeled antibody to the sample so that labeled and unlabelled forms compete for binding to the solid phase. Such assay techniques are well known and well described in both the patent and scientific literature. See, e.g., U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Enzyme-linked immunosorbent assay (ELISA) methods are described in detail in U.S. Pat. Nos. 3,791,932; 3,839,153; 3,850,752; 3,879,262; and 4,034,074. ELISA assays detect very low titers of autoantibodies.

Autoantibodies can also be detected by solid-phase radio-immunoassay (RIA). The solid phase is exposed to the serum sample in the presence of radio-labeled antibodies that compete for binding to the immobilized ligand. In this assay, the amount of radiolabel bound to the solid phase is inversely related to the amount of autoantibodies initially present in the serum sample. After separation of the solid phase, non-specifically bound radiolabel is removed by washing, and the amount of radiolabel bound to the solid phase determined. The amount of bound radiolabel is, in turn, related to the amount of autoantibodies initially present in the sample.

In one embodiment, the assay is performed in a flow-through or strip test format, wherein the 14-3-3 protein or fragment thereof is immobilized on a membrane, such as nitrocellulose. In the flow-through test, autoantibodies to 14-3-3 proteins within the sample bind to the immobilized 14-3-3 protein or fragment thereof as the sample contacts the membrane. A second, labeled binding agent then binds to the immune complex as a solution containing the second binding agent contacts the membrane. The detection of bound second binding agent may then be performed as described above. In the strip test format, one end of the membrane to which 14-3-3 protein or fragment thereof is bound is immersed in a solution containing the sample. The sample migrates along the membrane through a region containing second binding agent, e.g., to the autoantibodies, and to the area of immobilized 14-3-3 protein or fragment thereof. Concentration of second binding agent at the area of immobilized 14-3-3 protein or fragment thereof indicates the presence of an arthritic condition, or patient prognosis, etc. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of the autoantibody that would be sufficient to generate a positive signal in the assay, in the format discussed above. Preferred binding agents for use in such assays are 14-3-3 proteins and fragments thereof. Such tests can typically be performed with a very small amount of biological sample and at the point of care, which may also be quantifiable.

In addition to detecting the presence of autoantibodies in a sample, many methods can be used to quantitatively measure the levels of the autoantibodies. In some methods, the antigen reacts with the autoantibody in a liquid phase, and the autoantibodies are quantitatively measured by an immunoprecipitation technique. For example, a 14-3-3 protein or fragment thereof (i.e., full length isomer or antigenic fragments) can be detectably labeled (e.g., with an isotope or an enzyme). The polypeptides can be labeled during synthesis (e.g., by adding $^{35}$S-methionine to an in vitro translation system or cellular expression system) or after synthesis. The detectable antigen is added directly to a liquid biological sample (e.g., a serum) to form immune complexes. The immune complexes can be precipitated with polyethylene glycol. The immune complexes can also be isolated with a secondary antibody (e.g., goat anti-human immunoglobulin) or other kind of binding molecules (e.g., protein A or protein G) that is bound to a solid support (e.g., agarose or sepharose beads). The immunoprecipitates are washed several times after being separated from the liquid sample and examined for intensity of the detectable label (e.g., radioactivity). Any autoantibody present in the sample can thus be detected and quantified. Optionally, an unlabelled polypeptide can also be added to compete with the labeled polypeptide for binding to autoantibodies.

The diagnostic methods of the present invention are also directed to detecting in a subject circulating immune complexes formed between 14-3-3 proteins and an autoantibody. The methods discussed above can be readily modified for detection of such immune complexes. For example, an immobilized binding molecule (e.g., protein A or protein G bound to a bead) can be added to a liquid biological sample. After separation from the liquid phase, immune complexes captured by the binding molecules can be analyzed with SDS-PAGE and probed with various antibodies against 14-3-3 proteins. The captured antigens can also be subject to direct amino acid sequence analysis. Identity of the immune complexes can thus be revealed. A number of assays are routinely practiced to detect circulating immune complexes in a subject, e.g., as described in Tomimori-Yamashita et al., Lepr Rev, 70(3):261-71, 1999 (antibody-based enzyme-linked immunosorbent assay); Krapf et al., J Clin Lab Immunol, 21(4):183-7, 1986 (fluorescence linked immunosorbent assay); Kazeem et al., East Afr Med J, 67(6):396-403, 1990 (laser immunonephelometry); and Rodrick et al., J Clin Lab Immunol, 7(3):193-8, 1982 (Protein A-glass fiber filter assay, PA-GFF, and polyethylene glycol insolubilization assay). Each of these well known assays can be employed to detect circulating immune complexes for the methods of the present invention.

To improve clinical sensitivity, multiple markers may be assayed within a given sample. In particular, one or more other markers of arthritis, or prognostic indicators, etc., may be assayed in combination with autoantibodies to 14-3-3 protein. These other markers may be proteins or nucleic acids.

In a preferred embodiment, one or more of the other markers are matrix metalloproteinase (MMP) proteins or nucleic acids or other factors which are commonly used as indicators for arthritis, e.g., anti-cyclic citrullinated peptide (CCP), anti-rheumatoid factor (RF), c-reactive protein (CRP), serum amyloid A (SAA), interleukin 6 (IL-6), S100 calcium-binding proteins, osteopontin, RF, MMP-1, MMP-3, hyaluronic acid, soluble cluster of differentiation 14 (sCD14), angiogenesis markers and products of bone, cartilage or synovium metabolism (e.g., c-terminal crosslinking telopeptide of type I (CTX-I) and type II (CTX-II) collagen), etc. Methods for isolating and assaying nucleic acids based on reference sequences are well known in the art, as are methods for detecting proteins of interest within a patient sample.

Combination assays may be done concurrently or sequentially. The selection of markers may be based on routine experiments to determine combinations that results in optimal sensitivity.

In one embodiment, the invention provides methods for diagnosing an arthritic condition. In general, an arthritic condition may be detected in a patient based on the presence of autoantibodies to 14-3-3 in the synovial fluid, synovial joint, blood, plasma, or serum of a patient. In other words, autoantibodies to 14-3-3 protein may be used as a marker to indicate arthritis.

In addition, the presence of autoantibodies to 14-3-3, or the relative levels of autoantibodies to 14-3-3, as determined through the use of a 14-3-3 protein or fragment thereof may be a prognostic indicator of early-stage arthritis, before it progresses to a debilitating form. An advantage of early prognosis or diagnosis is earlier implementation of a treatment regimen.

To determine the presence or absence of an arthritic condition in a subject, the level of autoantibodies against, or immune complexes with, 14-3-3 in a biological sample from the subject may generally be compared to a level of autoantibodies/immune complexes corresponding to a normal control. In one preferred embodiment, the normal control is established from the average mean level of autoantibodies against, or immune complexes with, 14-3-3 in samples from patients without arthritis. In an alternative embodiment, the normal control value may be determined using a Receiver Operator Curve, for example see the method of Sackett et al., Clinical Epidemiology: A Basic Science for Clinical Medicine, Little Brown and Co., 1985, p. 106-7. Briefly, in this embodiment, the control value may be determined from a plot of pairs of true positive rates (i.e., sensitivity) and false positive rates (100%-specificity) that correspond to each possible cut-off value for the diagnostic test result. The control value on the plot that is the closest to the upper left-hand corner (i.e., the value that encloses the largest area) provides the most accurate value, and a sample generating a signal that is higher than the value determined by this method may be considered positive. Alternatively, the control value may be shifted to the left along the plot, to minimize the false positive rate, or to the right, to minimize the false negative rate. In general, a sample generating a signal that is higher than the control value determined by this method is considered positive for arthritis.

In one aspect, the invention provides methods for differentiating between subtypes of arthritis. In one embodiment, the methods involve determining the level of autoantibodies against, or immune complexes with, at least one 14-3-3 protein or fragment thereof. In a preferred embodiment, the level of autoantibodies/immune complexes to 14-3-3 in the patient is compared to that of samples from subjects whose subtype of arthritis is known and/or previously-established.

In one aspect, the invention provides methods for determining the response potential of a patient to treatment directed at arthritis. In one embodiment, the methods involve determining the level of autoantibodies against, or immune complexes with, at least one 14-3-3 protein or fragment thereof in a patient sample. In a preferred embodiment, the level of autoantibodies to/immune complexes with 14-3-3 in the patient sample is compared to that of samples from subjects whose ability to respond to treatment is known. A relatively high level of autoantibodies to/immune complexes with 14-3-3 in a first patient sample as compared to a sample from a non-inflammatory subject and/or a sample from another inflammatory patient may indicate the first patient is a preferred candidate for a well-known treatment, e.g., disease-modifying anti-rheumatic drug (DMARD) therapy such as anti-TNF, methotrexate, minocycline, hydroxychloroquine, sulphasalazine, azathioprine, anti-IL-1, anti-IL-6r, and the like. Conversely, a relatively low level of autoantibodies/immune complexes to 14-3-3 in a first patient sample as compared to a sample from another inflammatory patient may indicate the first patient is not a preferred candidate for a well-known treatment, especially if the level is closer to that of a sample from a non-inflammatory subject.

Treatment regimens for various types of arthritis are known in the art. For example, a patient diagnosed with rheumatoid arthritis may be prescribed non-steroidal anti-inflammatory medications (NSAIDs) initially, to ease the discomfort and reduce the inflammation. Other treatment regimens may include, for example, steroidal anti-inflammatory medications (SAIDs e.g. cortisol, prednisone), cyclooxygenase 2 specific inhibitors (CSIs), glucocorticoids, and/or standard disease-modifying anti-rheumatic drugs (DMARDs) such as, e.g., anti-TNF-alpha neutralizing agents, immunosuppressive drugs (e.g., cyclosporine, azathioprine, cyclophosphamide), antibiotics, antimalarials and cytotoxic drugs (e.g., methotrexate, sulfasalazine, leflunomide,). Treatment regimens may also advantageously include those that target 14-3-3 proteins directly, see, e.g., PCT/CA2008/002154. Details on dosage or examples of particular drugs will be known to those of skill in the art, and may be found in, for example Harrison's Principles of Internal Medicine 15th ed. BRAUNWALD et al eds. McGraw-Hill or "The Pharmacological basis of therapeutics", 10th edition. 5 HARDMAN H G., LIMBIRD L E. editors. McGraw-Hill, New York, and in "Clinical Oncology", $3^{rd}$ edition. Churchill Livingstone/Elsevier Press, 2004. ABELOFF, M D. editor.

In one aspect, the invention provides methods for monitoring treatment of arthritis. In one embodiment, the methods involve determining the level of autoantibodies against, or immune complexes with, at least one 14-3-3 protein or fragment thereof in patient samples and monitoring the level of autoantibodies to/immune complexes with 14-3-3 in a patient undergoing treatment.

The presence or relative levels of autoantibodies to/immune complexes with 14-3-3 may correlate with the presence or relative levels of other proteins known to be associated with arthritic conditions in patients. Nonlimiting examples of proteins well-known to be associated with an arthritic condition include inflammatory cytokines, such as tumor necrosis factor, 14-3-3 protein, and matrix metalloproteinases (MMPs), such as MMP-1 or MMP-3, etc. At least 25 different MMPs have been identified. Detection of autoantibodies to 14-3-3 in combination with detection of at least one inflammatory cytokine and/or MMP in a patient sample may be used to diagnose arthritis. Additionally, the presence or relative levels of autoantibodies/immune complexes to 14-3-3 in combination with at least one 14-3-3 isoform, at least one MMP and/or at least one inflammatory cytokine in a patient sample may be used as a prognostic indicator of early-stage arthritis, before the arthritis progresses to a debilitating form.

Also described herein are kits for evaluating an arthritic condition. Such kits typically comprise two or more components necessary for performing a diagnostic and/or prognostic assay. Components may be compounds, reagents, containers, instructions and/or equipment. For example, one container within a kit may contain a 14-3-3 protein or fragment thereof. Such kits may also contain a detection reagent as described above that contains a reporter group suitable for direct or indirect detection of antibody binding.

Accordingly, described herein are kits for detecting the presence of autoantibodies to/immune complexes with 14-3-3 and optionally other markers, e.g., MMPs, in a patient sample, the kit being useful for providing a diagnostic or prognostic result suitable for diagnosing or differentiating various arthritic conditions. Additional indications where the presence of 14-3-3 proteins and/or autoantibodies may be implicated also include, for example, cardiovascular and/or neurodegenerative disorders. A kit may comprise a 14-3-3 protein or fragment thereof, which may optionally be detectably labeled, e.g., with a radioactive label, a luminescent label, a fluorescent label, an enzyme, etc.

Methods for detectably labeling proteins are well-known in the art. Such a kit may further include detection reagents specific for other markers of arthritis e.g., anti-CCP, anti-RF, CRP, SAA, IL-6, S1OO, osteopontin, RF, MMP-I, MMP-3, hyaluronic acid, sCD14, angiogenesis markers and products of bone, cartilage or synovium metabolism (e.g., CTX-I and CTX-II), etc. The kit may further include other secondary reagents necessary for the detection of autoantibodies to 14-3-3 immunologically, such as labeled secondary antibodies (e.g. anti-human antibodies), chromogenic or fluorogenic reagents, polymerization agents and the like. Instructions for using the kit for diagnostic or prognostic purposes, including appropriate comparison standards for quantifying and/or evaluating the level of such autoantibodies in the context of a particular disease state, may also be advantageously provided in printed form and/or recorded on a suitable media.

EXPERIMENTAL

Example 1

Detection of Recombinant 14-3-3 Eta with Human Serum

Recombinant 14-3-3 Eta protein (Augurex, North Vancouver, BC, Canada) was loaded onto an SDS-PAGE gel and transferred to a nitrocellulose membrane. Human sera from subjects not diagnosed with rheumatoid arthritis (Biochemed, Winchester, Va.) or subjects diagnosed with rheumatoid arthritis (Biochemed, Suffolk County, N.Y.) were incubated with the membrane to detect and characterize autoantibodies for 14-3-3 Eta in sera. Autoantibodies were detected using an anti-human secondary antibody conjugated to HRP (Jackson ImmunoResearch Laboratories, West Grove, Pa.) and visualized by chemiluminescence.

In particular, 2 μg of recombinant 14-3-3 Eta protein in sample buffer (62.5 mM Tris acid, 2% SDS, 10% glycerol, 0.01% bromophenol blue, 5% β-mercaptoethanol) was loaded onto a 15% SDS-PAGE gel. The SDS-PAGE gel was run with running buffer (2.5 mM Tris base, 19.2 mM glycine, 0.1% SDS) at 70 volts for 30 minutes, then 140 volts until the dye front reached the bottom of the gel. Protein was then transferred with transfer buffer (2.5 mM Tris base, 19.2 mM glycine, 20% methanol) on ice for 400 mAh to a nitrocellulose membrane. Transfer efficiency was verified using Ponceau S dye to visualize proteins on membrane. Membranes were then placed in blocking buffer (5% nonfat dry milk in TBS-T (10 mM Tris, pH 7.5, 150 mM NaCl, 0.05% Tween20)) and incubated on shaker for 1 hour at room temperature. Blocking buffer was removed and human sera diluted with blocking buffer (1:5, 1:10, 1:20, 1:50, 1:100, v/v) was added to cut membranes. Membranes were incubated on shaker overnight at 4° C. Membranes were then washed 3 times for 5 minutes each with TBS-T. Anti-human HRP antibody (0.1 μg/ml) in blocking buffer was then added and incubated on shaker for 1 hour at room temperature. Membranes were then washed 6 times for 5 minutes each with TBS-T. Auto-antibodies were visualized using SuperSignal West Pico Chemiluminescent Substrate (Pierce, Rockford, Ill.) and recorded onto film.

Figure 2:
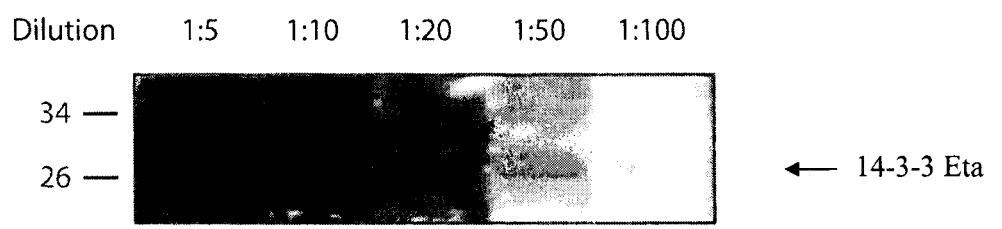
FIG. 2 shows a western blot of recombinant 14-3-3 Eta using serial dilution of serum from a patient diagnosed with rheumatoid arthritis (Sample 3365).

The representative data presented in FIGS. 1 and 2 demonstrate that human serum taken from patients with arthritis possess antibodies that are directed towards 14-3-3 eta, as is evidenced by the visualization of recombinant 14-3-3 eta by immunoblot analysis.

Figure 3:
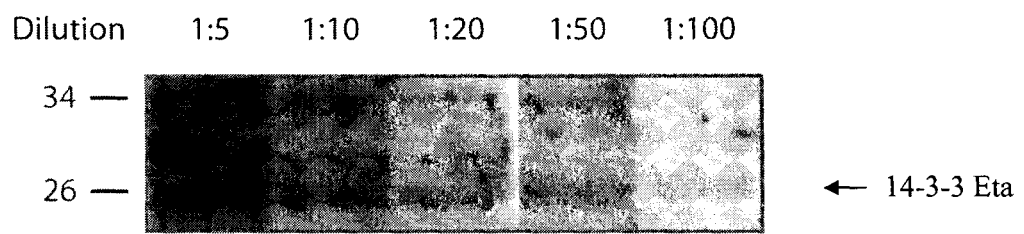
FIG. 3 shows a western blot of recombinant 14-3-3 Eta using serial dilution of serum from a patient not diagnosed with rheumatoid arthritis (Sample 40).
Figure 4:
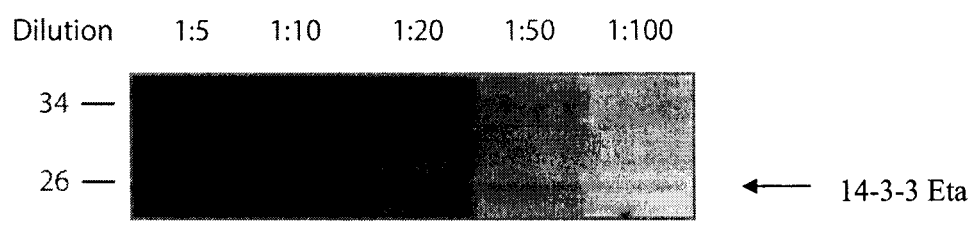
FIG. 4 shows a western blot of recombinant 14-3-3 Eta using serial dilution of serum from a patient not diagnosed with rheumatoid arthritis (Sample 39).

The presence of these auto-antibodies appears to be a specific phenomenon in inflammatory conditions like arthritis, as these auto-antibodies were not detectable or were detectable at lower levels in serum taken from normal healthy individuals (FIGS. 3 and 4).

As part of the natural defense mechanism, the immune system generates antibodies as a means of destroying foreign particles/pathogens it encounters. In the case of arthritis, it is well established that 14-3-3 proteins, mainly 14-3-3 eta and gamma, are detectable in the synovial fluid and serum. Currently, it is believed that the levels of 14-3-3 protein and/or autoantibody to 14-3-3 protein or fragments thereof in the synovial fluid and serum directly correlate to joint tissue damage, and that such correlation may be used in the methods described herein. For example, an increased level of autoantibody to 14-3-3 may lead to a reduction in 14-3-3 protein, and thus correlate with a lower level or risk of joint tissue damage.

This study was performed to determine whether the immune system attempts to counteract or respond to the presence of 14-3-3, by specifically generating an antibody response to target and clear them from serum. The presence of these autoantibodies would provide further evidence that these proteins do not normally exist in the extracellular space, as the body would not mount such a response if they were normally present.

The data clearly demonstrates that in the case of arthritis, autoantibodies targeted to 14-3-3 are present at higher levels in comparison to serum from normal healthy individuals. Accordingly, the differential expression of these antibodies in comparison to normal healthy individuals may be useful in terms of diagnosing arthritis. Furthermore, the differential expression may have utility in the prognosis of the disease as well as defining which therapy to administer to a patient as well as monitoring a patient's response to a given therapy.

Example 2

Development of an Assay to Measure the Titres or Levels of Anti-14-3-3-Antibodies In order to map the 14-3-3 epitopes most commonly recognized by autoantibodies, overlapping 15-residue peptides representing the entire sequence of 14-3-3 eta peptide will be synthesized directly on cellulose paper using the spot synthesis technique. Cysteine residues will be replaced with serine in order to reduce the chemical complications caused by the presence of cysteines. Cellulose membranes modified with polyethylene glycol and Fmoc-protected amino acids will be purchased from Abimed (Lagenfeld, Germany). The array will be defined on the membrane by coupling a β-alanine spacer and peptides will be synthesized using standard DIC (diisopropylcarbodiimide)/HOBt (hydroxybenzotriazole) coupling chemistry as described previously (Molina et al. (1996) *Peptide Research* 9: 151-155; Frank et al. (1992) *Tetrahedron* 48: 9217-9232).

Activated amino acids will be spotted using an Abimed ASP 222 robot. Washing and deprotection steps will be done manually and the peptides will be N-terminally acetylated after the final synthesis cycle. Following peptide synthesis, the membrane will be washed in methanol for 10 minutes and in blocker (e.g., TBST (Tris-buffered saline with 0.1% (v/v) Tween™ 20) and 1% (w/v) casein). After washing, the membrane will be incubated with serum obtained from a patient diagnosed with Rheumatoid arthritis with gentle shaking. After washing with blocker 3 times, the membrane will be incubated with HRP-labeled secondary antibody. The membrane will be washed three times for 10 minutes each with blocker and 2 times for 10 minutes each with TBST. Bound antibody will be visualized using SuperSignal™ West reagent (Pierce) and a digital camera (Alphananotech Fluoromager).

Epitope mapping for a 14-3-3 peptide will be performed with serum from at least three different patients, each diagnosed with arthritis and confirmed as having anti-14-3-3 autoantibodies, to determine the commonly recognized epitopes. Additionally, epitope mapping may be performed with another, if not all, 14-3-3 isoforms to determine whether the commonly recognized epitope is specific to one isoform, e.g., 14-3-3 eta, or shared with one, two, three, four, five, or six other 14-3-3 isoforms.

The commonly recognized epitope(s) of at least 14-3-3 eta will be synthesized and used to evaluate the specificity of the epitope(s) for evaluating and/or characterizing an arthritic condition, particularly Rheumatoid Arthritis, compared to other arthritic subtypes and/or healthy controls. After specificity for evaluating and/or characterizing an arthritic condition is established, the commonly recognized epitope(s) will be developed into a quantitative assay that measures the level of 14-3-3 autoantibodies in a patient sample. The assay may then be used to detect and/or quantify autoantibodies to 14-3-3 protein in a patient sample.

All references and patents cited herein are expressly incorporated herein in their entirety by reference.

I claim:

1. A method for diagnosing Rheumatoid Arthritis in a subject, comprising:
   a) obtaining a test biological sample from a subject suspected of having or at risk for developing Rheumatoid Arthritis;
   b) detecting the amount of an autoantibody against 14-3-3 eta protein or fragment thereof in said test biological sample, wherein said detection is performed by contacting the test biological sample with a 14-3-3 eta fragment consisting of a 14-3-3 eta epitope selected from the group consisting of SEQ ID NOs:1-29, and 31-32, under a condition suitable for the formation of at least one immune complex between the 14-3-3 eta fragment and the autoantibody specific for said 14-3-3 eta epitope that may be present in the biological sample;

c) comparing the amount of the autoantibody in the test biological sample against the amount of the autoantibody in a normal control biological sample;

d) diagnosing the subject as having Rheumatoid Arthritis based on the presence of a larger quantity of the autoantibody in the test sample as compared to the normal control sample.

2. The method of claim 1, wherein the test biological sample is selected from the group consisting of blood, synovial fluid, plasma, serum and tissue.

3. The method of claim 1, wherein the 14-3-3 eta fragment is detectably labeled with a label selected from the group consisting of a radioactive label, a luminescent label, a fluorescent label, and an enzyme.

4. The method of claim 1, wherein contacting the test biological sample with at least one 14-3-3 eta fragment involves contacting the test biological sample with the 14-3-3 eta fragment, wherein the 14-3-3 eta fragment is bound to a solid support.

5. The method of claim 4, wherein said solid support is a test well in a microtiter plate or a nitrocellulose or other suitable membrane.

6. The method of claim 4, wherein said solid support is a bead or disc.

7. The method of claim 6, wherein said bead or disc is comprised of a material selected from the group consisting of glass, fiberglass, latex and a plastic material.

8. The method of claim 7, wherein said plastic material is polystyrene.

9. The method of claim 7, wherein said plastic material is polyvinylchloride.

10. The method of claim 4, wherein the 14-3-3 fragment bound to said solid support reacts with the autoantibody in a liquid phase.

11. The method of claim 1, wherein the autoantibody is detected by an ELISA assay.

12. The method of claim 1, wherein said detection occurs by chemiluminescence.

13. The method of claim 1, further comprising detection of at least one additional arthritis marker in said test biological sample, wherein said at least one additional arthritis marker is selected from the group consisting of 14-3-3-eta protein, matrix metalloproteinase-1 (MMP-1), MMP-3, anti-cyclic citrullinated peptide (CCP), rheumatoid factor (RF), c-reactive protein (CRP), serum amyloid A (SAA), interleukin 6 (IL-6), S100 calcium-binding protein, osteopontin, hyaluronic acid, soluble cluster of differentiation 14 (sCD14), c-terminal crosslinking telopeptide of type I (CTX-I) and type II (CTX-II) collagen.

14. The method of claim 1, wherein said 14-3-3 eta epitope is selected from the group consisting of SEQ ID NOs: 1, 2, 9, 11, 13, 15, 17, 18, 22, 23, 25, and 28.

* * * * *